United States Patent
Bednar et al.

(10) Patent No.: US 8,518,709 B2
(45) Date of Patent: Aug. 27, 2013

(54) METHOD FOR REGENERATING A BIOSENSOR

(75) Inventors: Sonja Bednar, Gundelfingen (DE); Johannes Baader, Freiburg (DE); Holger Klapproth, Freiburg (DE); Ingo Freund, Freiburg (DE)

(73) Assignee: Endress+Hauser Conducta Gesellschaft fuer Mess-und Regeltechnik mbH+Co. KG, Gerlingen (DE)

( * ) Notice: Subject to any disclaimer, the term of this patent is extended or adjusted under 35 U.S.C. 154(b) by 707 days.

(21) Appl. No.: 12/619,871

(22) Filed: Nov. 17, 2009

(65) Prior Publication Data

US 2010/0129894 A1    May 27, 2010

(30) Foreign Application Priority Data

Nov. 21, 2008   (EP) .................................. 08020280

(51) Int. Cl.
*G01N 21/00* (2006.01)
(52) U.S. Cl.
USPC ............... 436/164; 422/82.11; 435/288.7; 435/808; 436/518; 436/524; 436/525; 436/805
(58) Field of Classification Search
None
See application file for complete search history.

(56) References Cited

U.S. PATENT DOCUMENTS 6,087,112 A * 7/2000 Dale ........................... 435/6.14
7,101,669 B2 * 9/2006 Thompson et al. ........... 435/6.11

FOREIGN PATENT DOCUMENTS

| DE | 19808003 C2 | 4/2000 |
| EP | 1078248 B1 | 7/2005 |
| EP | 080202807 | 7/2009 |
| JP | 2006197836 | 8/2006 |
| WO | 9958963 A1 | 11/1999 |
| WO | 0179535 A2 | 10/2001 |
| WO | 2006073504 A2 | 7/2006 |

OTHER PUBLICATIONS

Wu, H. et al., Reuse of cDNA microarrays hybridized with cRNA by stripping with RNase H, Nov. 2008, pp. 573-575.
Furtado, L. Michelle et al. Activity of Lamda-Exonuclease on Surface-Attached Oligonucleotide Detected by Acoustic Wave Device and Radiochemical Labeling, 2008, pp. 2805-2818.
Horacek, J. et al. Characterization of the interactions between immobilized parathion and the corresponding recombinant SCFV antibody using a piezoelectric biosensor, 1998, pp. 363-374.
Brecht, Andreas et al. A direct optical immunosensor for atrazine detection, 1995, pp. 289-299.
Kroeger, K. et al. Versatile biosensor surface based on peptide nucleic acid with label free and total internal reflection fluorescence detection for quantification of endocrine disruptors, 2002, pp. 37-48.

(Continued)

*Primary Examiner* — Chris L Chin
(74) *Attorney, Agent, or Firm* — The Webb Law Firm, P.C.

(57) ABSTRACT

In a method for regenerating a biosensor, a biosensor is prepared having a substrate surface on which at least one receptor is immobilized. At least one ligand that is binding specific to the receptor is bound to the receptor, said ligand, together with the receptor, forming a ligand-receptor complex. To regenerate the biosensor, the ligand-receptor complex is brought into contact with an enzyme. The enzyme is selected so that it catalyzes the ligand into fragments. The enzyme is inert with respect to the receptor.

3 Claims, 6 Drawing Sheets

(56) References Cited

OTHER PUBLICATIONS

Halamek et al. Development of a biosensor for glycated hemoglobin, 2007, pp. 1127-1133.

Lee Hye Jin et al. Fabricating RNA micrarrays with RNA-DNA surface ligation chemistry, 2005, pp. 7832-7837.

Hu Zhiyuan et al. High reproducibility using sodium hydroxide-stripped long oligonucleotide DNA microarrays, Jan. 2005, pp. 121-124.

Hahnke et al. Striptease on glass: Validation of an improved stripping procedure for in situ microarrays, 2007, pp. 1-13.

* cited by examiner

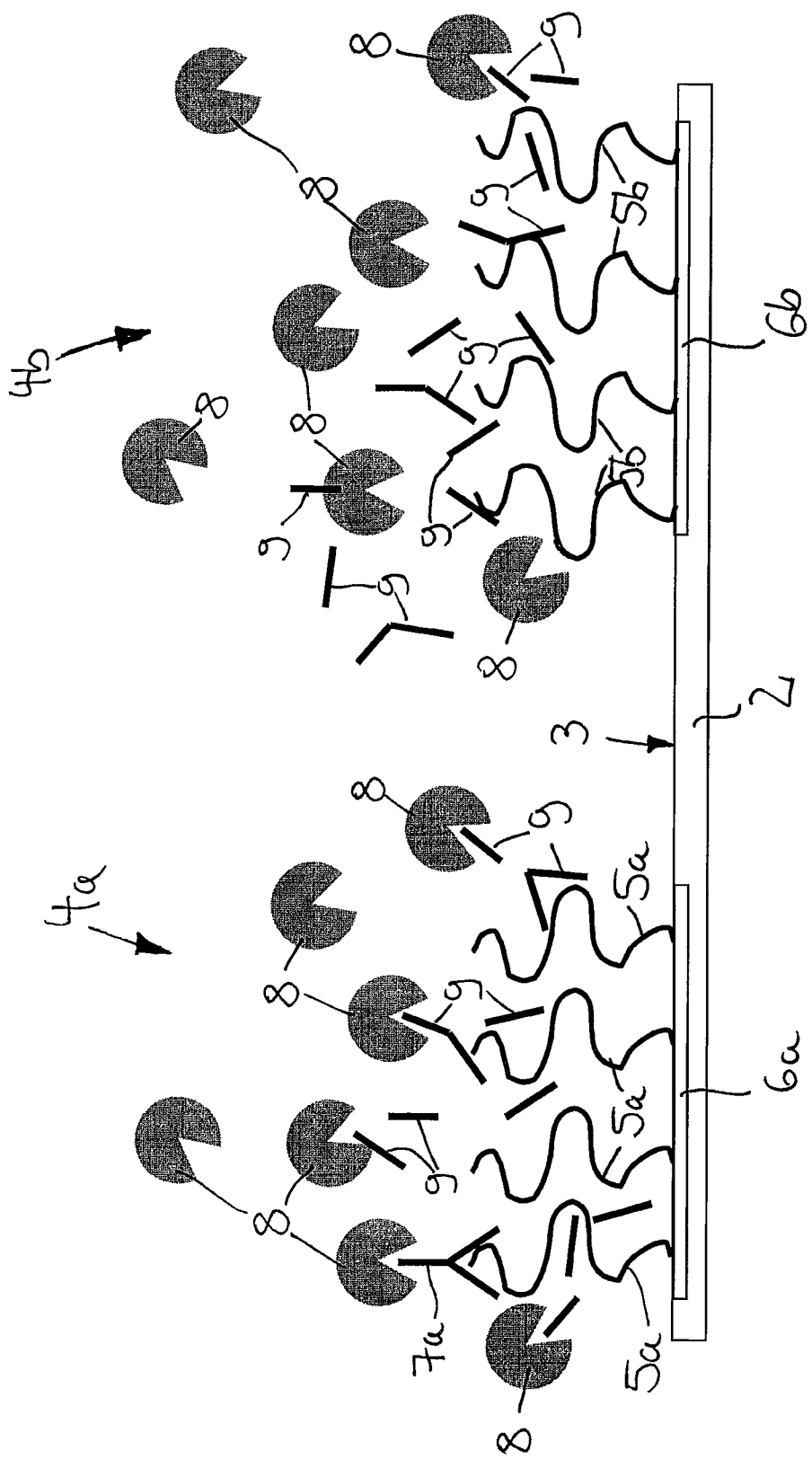

METHOD FOR REGENERATING A BIOSENSOR

The invention involves a method for regenerating a biosensor wherein a biosensor is prepared, said biosensor having a substrate surface on which at least one receptor is immobilized, to which at least one ligand that binds specifically to the receptor is bound forming a ligand-receptor complex, and wherein the biosensor is regenerated in that the ligand is separated from the receptor.

Such a method is familiar from EP 1 078 248 B1. In that method, first a biosensor is prepared, said biosensor having a substrate surface on which 22-mer oligonucleotides are immobilized as receptors. The receptors are covalently bound to reactive groups of an epoxy silane located on the substrate surface. The substrate surface is rinsed with a buffer solution having a pH of 7.75. Then, a sample to be tested is applied to the substrate surface containing a ligand to be detected having a concentration that is known. The ligand is a complementary 22-mer oligonucleotide tagged with an optical marker. The amount of time the ligand is in contact with the substrate surface is chosen to be long enough that the ligand can bind to the receptor. Then, fluorescent radiation that depends on the binding of the ligand to the receptor is generated and measured using an optical sensor. The measured value obtained in this manner is saved.

Now, the substrate is rinsed with the buffer solution and the dissociation rate of the DNA hybrid located on the surface is determined. In an additional process step, the substrate surface makes contact with 10 mM of a sodium hydroxide solution to separate the ligands bound to the receptors from the receptors thereby regenerating the biosensor. The biosensor is now calibrated again in the buffer solution and whether the receptors were completely regenerated is verified.

The method has the disadvantage that the ligands may be damaged by contact with the sodium hydroxide solution. In particular, the binding affinity of the receptors for the ligands may abate during the regeneration step. It may also occur that, through the use of the sodium hydroxide solution, not all ligands may be separated from the receptors. In addition, the optical sensor and/or electrical components that come into contact with the sodium hydroxide solution may be damaged.

In the case of another method of the aforementioned type known in practice, the biosensor is regenerated by heating. In this method, the temperature is increased to the extent that the ligands bound to the receptors separate from the receptors. The receptors can also be damaged in this method. The method is primarily used for DNA receptors. The method is suitable only to a very limited extent for protein receptors because protein receptors denature rapidly at increased temperature and are then no longer binding specific for the ligands.

For this reason, the objective is to create a method of the aforementioned type that allows regeneration of the biosensor after the ligand has bonded to the receptor. In this respect, the sensitivity of the biosensor should be retained to the maximum extent possible.

This objective is achieved in that the ligand-receptor complex is brought into contact with an enzyme for regeneration and in that the enzyme is selected such that it catalyzes the ligand into fragments and is inert with respect to the receptor.

Surprisingly, it was determined that using such an enzyme is possible in a simple way to separate the ligands almost completely from the receptors they are bound to without damaging the receptors in this process. Even the ligand group bound to the receptor can be separated from the receptor using the enzyme. Subsequently, the enzyme and/or the fragments of the ligand can be simply removed from the substrate surface, for example, by applying a rinsing liquid to the substrate surface to rinse away the fragments and the enzyme. Using the method, it is possible to clean a biosensor, for example, after performing an assay, and to reuse it to detect a ligand in samples to be tested and/or to measure the ligand concentration. In this process, the biochip can even be cleaned or used several times if necessary. The method of this invention can also be used to clean biochips of contamination, e.g., with proteins, before being used for the first time following storage and/or transport (e.g., shipping).

It is advantageous if the ligand and the receptor belong to different substance classes. As a result of the different structure of the receptor and the ligand coming from this, the receptor is particularly insensitive to the enzyme in whose presence the ligand decomposes. Consequently, the biosensor can be regenerated in an even gentler manner.

In one preferred embodiment of the invention, the receptor is a ribonucleic acid, a protein and/or a peptide nucleic acid and the ligand is a deoxyribonucleic acid with the enzyme being a deoxyribonuclease. A deoxyribonuclease is understood to mean an enzyme that decomposes deoxyribonucleic acid strings, for example, an exonuclease and/or an endonuclease.

In another advantageous embodiment of the invention, the receptor is a protein, a deoxyribonucleic acid and/or a peptide nucleic acid and the ligand is a ribonucleic acid with the enzyme being a ribonuclease. A ribonuclease is an enzyme that decomposes ribonucleic acid strings, for example, ribonuclease A, which decomposes free ribonucleic acid strings, and/or ribonuclease B that decomposes ribonucleic acid strings bound to deoxyribonucleic acid.

In another advantageous embodiment of the invention, the receptor is a biotin and the ligand is a streptavidin with the enzyme being a proteinase. A proteinase is understood to mean an enzyme that splits protein or peptide and decomposes them into their individual parts, for example, proteinase K and/or peptidase.

However, it is also possible for the receptor to be a polysaccharide, a lipid, a digoxigenin and/or a carbohydrate and the ligand to be a protein, in particular an antibody, and the enzyme to be a proteinase. In this case, the antibody may be a lectin, for example.

In one preferred embodiment of the invention,
at least one biosensor is prepared having a substrate surface on which at least one receptor that is binding specific for the ligand is immobilized,
wherein a first sample containing the ligand in a known first concentration is brought into contact with the receptor such that at least one ligand binds to the receptor and can form a ligand-receptor complex with said receptor,
wherein at least one first value that is dependent on the binding of the ligand to the receptor is measured,
wherein the biosensor is subsequently regenerated,
wherein then a second sample containing the ligand in a second concentration to be determined is brought into contact with the receptor such that at least one ligand can bind to the receptor and can form a ligand-receptor complex with said receptor,
wherein at least one second value that is dependent on the binding of the ligand to the receptor is measured,
and that, with the help of these measured values and the known first concentration, the second concentration to be specified is determined. In this way, it is possible to calibrate the biosensor exactly and consequently to determine the concentration of the ligands in the second sample with great precision.

In the following, one exemplary embodiment of the invention is described in more detail using the drawings:

FIG. 6 illustrates the biosensor shown in FIG. 5 after the ligands have been fragmented in the presence of the enzyme.

Figure 1:
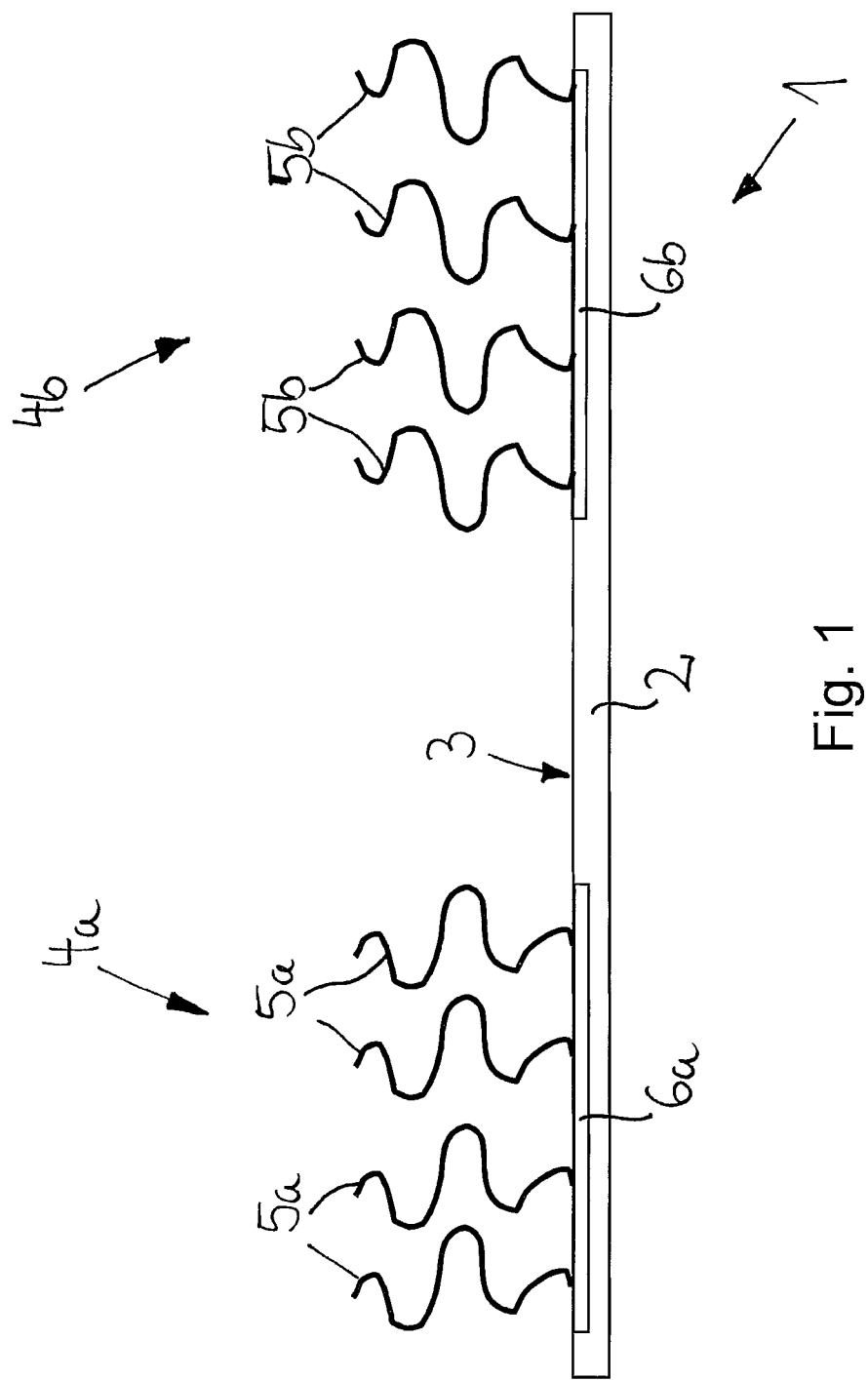
FIG. 1 shows a side view of a biosensor having a substrate with receptors immobilized on the surface of said substrate.

In one method for regenerating biosensors, a biosensor 1 having a substrate 2 with a plurality of test sites 4a, 4b on the substrate surface 3 is prepared with receptors 5a, 5b of different receptor types immobilized at these sites (FIG. 1). The receptors 5a, 5b are each pneumococcal polysaccharides. The different types of receptors are identified as PS1 to PS9 in FIGS. 2 and 3.

The substrate 2 essentially consists of a semiconductor material, preferably silicon. The substrate 2 has a silane layer, not shown in more detail in the drawing, on the substrate surface 3, the first binding sites of the receptors 5a, 5b being covalently bound to this layer.

It can be seen in FIG. 1 that the sensors 6 are integrated into the substrate 2 at the test sites 4a, 4b below the receptors and 5a, 5b. The sensors 6 are sensitive to a luminescent radiation still to be explained in more detail.

It is also conceivable that the substrate 2 consists of the semiconductor material only in areas, in particular at those points where the sensors 6 are located. In addition, it is possible to configure the sensors 6 outside the substrate 2. In this case, the substrate 2 may also consist of a different material suitable for immobilizing the receptors 5a, 5b, for example, glass, ceramic or plastic.

A free-flowing first sample is applied to the substrate surface 3, which sample contains the ligands 7a, 7b of different ligand types, each in a known concentration. Each ligand 7a, 7b is binding specific for one of the receptors 5a, 5b immobilized on the substrate 2. The receptors 5a, 5b also possess at least one second binding site at which the binding specific ligand 7a, 7b can bind to the appropriate receptor 5a, 5b.

The first sample can, for example, be produced in that specific quantities of the individual ligands 7a, 7b are diluted with a predetermined quantity of an aqueous solvent.

Figure 4:
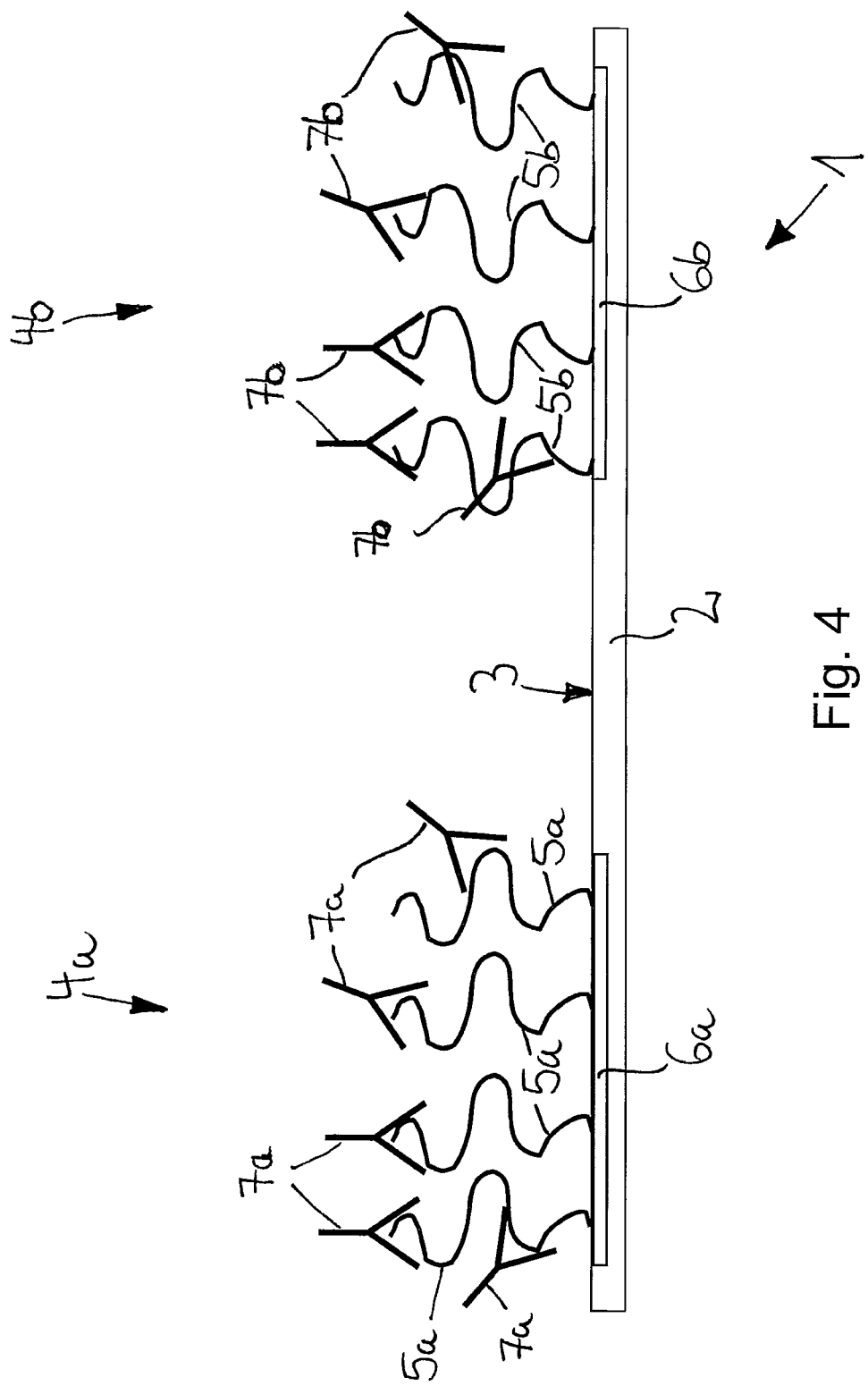
FIG. 4 depicts a biosensor with ligands bound to its receptors.

The amount of time the first sample is in contact with the receptors 5a, 5b is chosen to be long enough that a ligand 7a, 7b binds to virtually all second binding sites of the receptors 5a, 5b. The resulting receptor-ligand complexes are shown in FIG. 4.

Subsequently, any unbound receptors 5a, 5b are removed from the substrate surface 3, for example, using a rinsing solution. Then, detection antibodies are bound to the receptor-ligand complexes remaining on the substrate surface 3, which antibodies are tagged via streptavidin with an optical marker, namely biotin (sandwich ELISA). In an additional step, any free detection antibodies and any unbound streptavidin are removed from the substrate surface 3.

Figure 2:
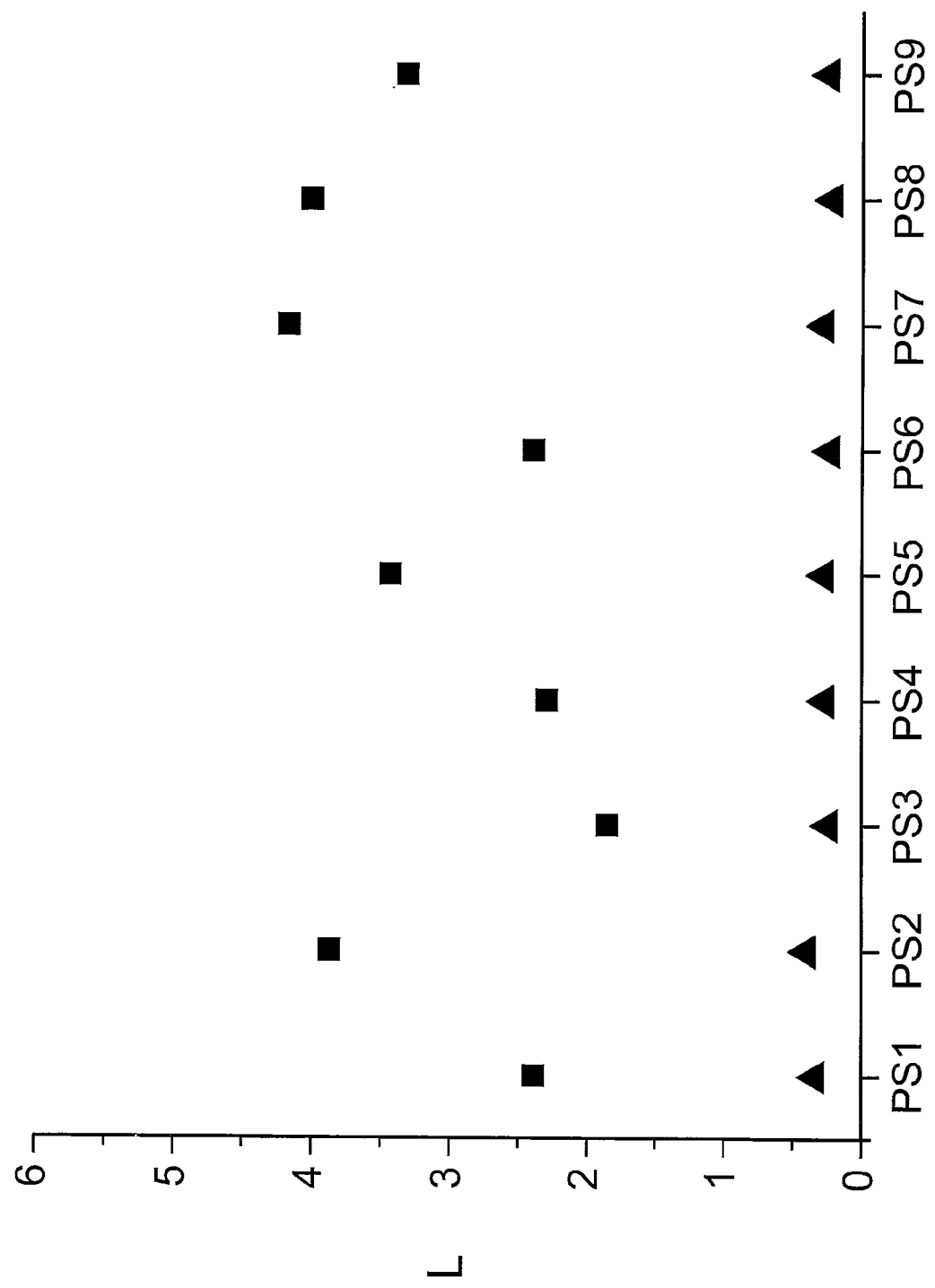
FIGS. 2 and 3 are graphs of measured values that are each a function of the binding of ligands to receptors of a specific receptor type with the receptor type plotted along the abscissa and the measured value plotted along the ordinate.

The receptor-ligand detection antibody biotin complexes remaining on the substrate surface are brought into contact with a streptavidin-conjugated horseradish peroxidase solution. Following addition of a chemiluminescent substrate, the horseradish peroxidase is excited to emit luminescent radiation by way of a chemical reaction. This radiation is measured using each of the sensors 6a, 6b configured at the appropriate test site 4a, 4b. The individual test sites are located far enough away from each other so that the luminescent radiation emitted by one test site is not visible to the sensors of adjacent test sites 4b, 4a. The first values measured in this manner are shown in FIG. 2 using squares. It can clearly be seen that the individual sensors 6a, 6b each have one measured signal.

Figure 5:
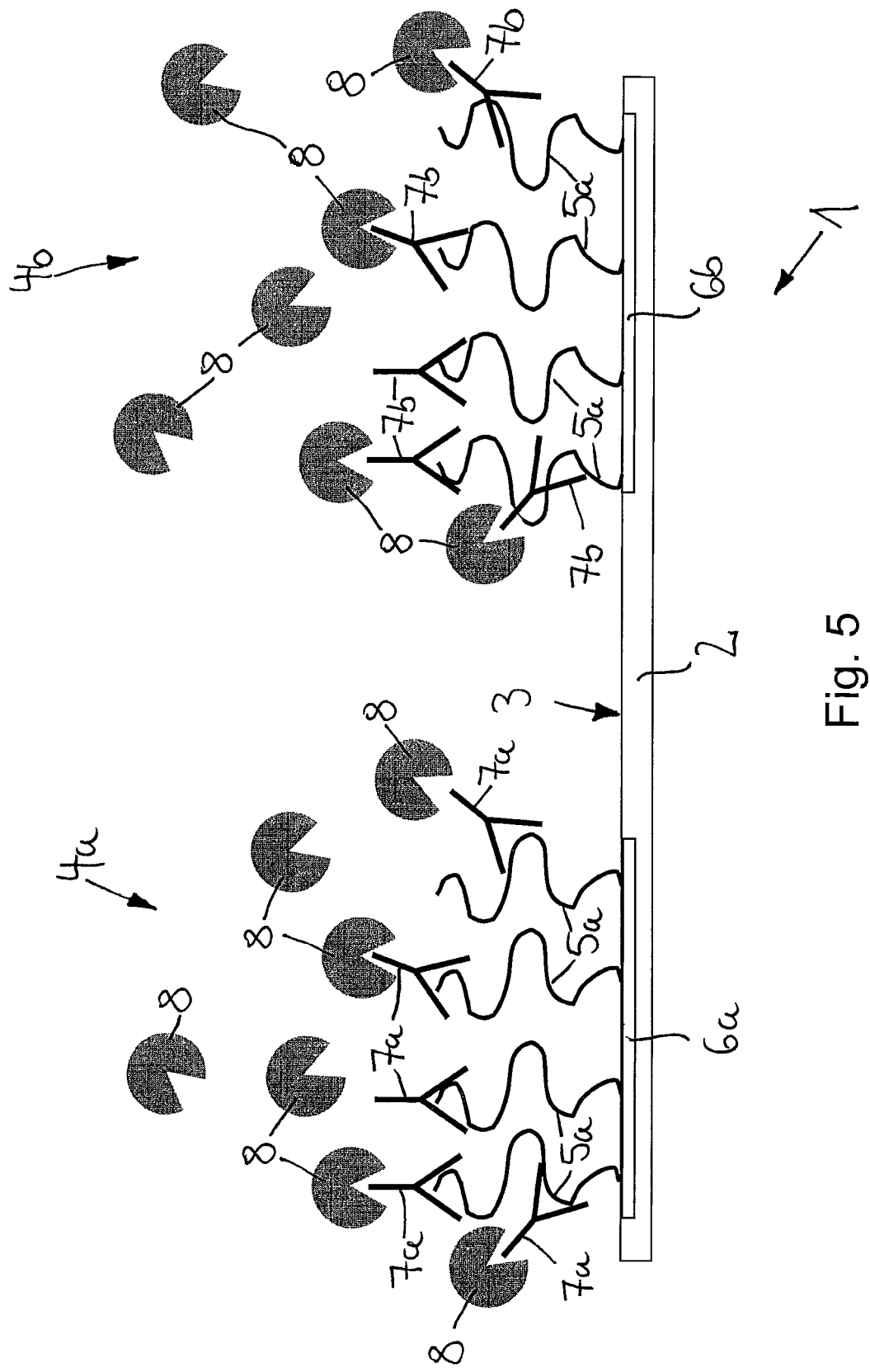
FIG. 5 shows the biosensor illustrated in FIG. 4 after being brought into contact with an enzyme in whose presence the ligands are fragmented, decomposed into monomers and digested.

After the values are measured in this way, the substrate surface 3 is rinsed and brought into contact with a solution containing proteinase K enzyme 8 for about 4 hours at a temperature of about 56° C. (FIG. 5). The enzyme 8 is selected such that the ligands 7a, 7b catalyze into fragments in the presence of the enzyme 8. However, the enzyme 8 is inert with respect to the receptors 5a, 5b, i.e., the receptors 5a, 5b are not changed by the presence of the enzyme. The enzyme 8 is commercially available, for example, from Sigma-Aldrich™, Saint Louis, Mo., 63103 USA, under catalog number P2308.

As can be seen in FIG. 6, the ligands 7a, 7b are completely separated from the second binding sites of the receptors 5a, 5b by the fragmentation. After fragmentation has finished, the fragments 9 and the enzyme are rinsed from the substrate surface 3 so that only the receptors 5a, 5b remain on the substrate surface 3 (FIG. 1).

To verify the effect of this cleaning, another test is performed using the cleaned biosensor 1. In this test, a buffer solution is applied to the substrate surface in place of the first sample, which solution contains no ligands 7a, 7b. Then, the biosensor 1 is brought into contact with a solution of biotin-tagged detection antibodies. After an additional rinsing step, the biosensor 1 is exposed to streptavidin-conjugated horseradish peroxidase solution. Then, the chemiluminescent substrate is brought into contact with the immobilized receptors 5a, 5b again and values are again measured using the sensors 6a, 6b. These are shown in FIG. 2 using triangles. It can clearly be seen that luminescent radiation no longer occurs with the exception of background radiation. The ligands 7a, 7b thus were completely removed from the receptors 5a, 5b.

After the chemiluminescent substrate was removed from the substrate surface 3 of the cleaned biochip, a second sample to be tested that presumably contains ligands 7a, 7b is applied to the substrate surface 3. The amount of time the second sample is in contact with the receptors 5a, 5b is chosen to be long enough that the ligands 7a, 7b can bind to the receptors 5a, 5b.

Subsequently, any unbound receptors 5a, 5b are removed from the substrate surface 3 and detection antibodies are bound to the receptor-ligand complexes remaining on the substrate surface 3, these antibodies being tagged with biotin. In an additional step, any free detection antibodies and any unbound biotin are removed from the substrate surface 3, for example by rinsing.

The receptor-ligand detection antibody biotin complexes remaining on the substrate surface 3 are brought into contact with a streptavidin-conjugated horseradish peroxidase solution. Following addition of a chemiluminescent substrate, the horseradish peroxidase is excited to emit luminescent radiation by way of a chemical reaction. Second values are measured using the sensors 6a, 6b.

Figure 3:
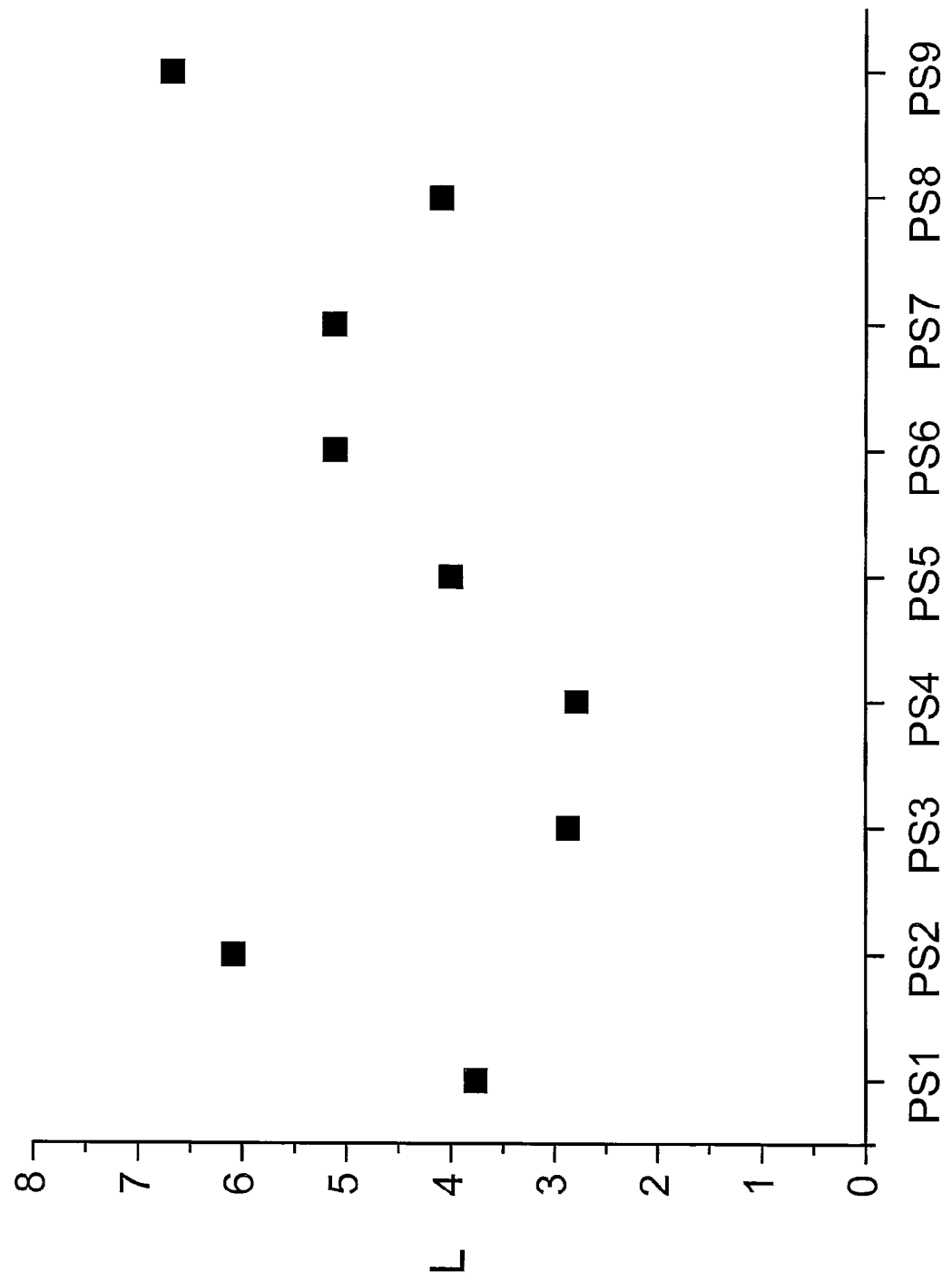

The second measured values are shown in FIG. 3 using squares. Comparing FIG. 2 to FIG. 3 clearly shows that the sensitivity of the biosensor 1 has been retained to the maximum extent possible during regeneration of the biosensor 1.

Using the first measured values, the second measured values and the known concentrations of the ligands 7a, 7b contained in the first sample, the concentrations of the ligands 7a, 7b are determined in the second sample.

If needed, the biosensor 1 can be regenerated again at least once to then determine measured concentration values for the ligands 7a, 7b for at least one additional sample.

The invention claimed is:

1. A method for regenerating a biosensor wherein a biosensor is prepared, said biosensor having a substrate surface on which at least one receptor is immobilized, to which at least one ligand that binds specifically to the receptor is bound, said ligand, together with the receptor, forming a ligand-receptor complex and wherein the biosensor is regenerated in that the ligand is separated from the receptor, the method comprising the steps of:
    bringing the ligand-receptor complex for regeneration into contact with an enzyme, and
    selecting the enzyme so that the enzyme catalyzes the ligands into fragments and the enzyme is inert with respect to the receptor,
    wherein the receptor is a biotin and the ligand is a streptavidin and that the enzyme is a proteinase.

2. A method for regenerating a biosensor wherein a biosensor is prepared, said biosensor having a substrate surface on which at least one receptor is immobilized, to which at least one ligand that binds specifically to the receptor is bound, said ligand, together with the receptor, forming a ligand-receptor complex and wherein the biosensor is regenerated in that the ligand is separated from the receptor, the method comprising the steps of:
    bringing the ligand-receptor complex for regeneration into contact with an enzyme, and
    selecting the enzyme so that the enzyme catalyzes the ligands into fragments and the enzyme is inert with respect to the receptor, wherein the receptor is a polysaccharide, a lipid, a digoxigenin and/or a carbohydrate and the ligand is a protein, and that the enzyme is a proteinase.

3. A method for regenerating a biosensor wherein a biosensor is prepared, said biosensor having a substrate surface on which at least one receptor is immobilized, to which at least one ligand that binds specifically to the receptor is bound, said ligand, together with the receptor, forming a ligand-receptor complex and wherein the biosensor is regenerated in that the ligand is separated from the receptor, the method comprising the steps of:
    bringing the ligand-receptor complex for regeneration into contact with an enzyme, and
    selecting the enzyme so that the enzyme catalyzes the ligands into fragments and the enzyme is inert with respect to the receptor, further comprising the steps of:
        immobilizing at least one receptor on a substrate of at least one biosensor wherein said at least one receptor is binding specific for the ligands,
        bringing into contact a first sample containing the ligand in a known first concentration with the receptor such that at least one ligand binds to the receptor and forms a ligand-receptor complex with said receptor,
        measuring at least one first value that is dependent on the binding of the ligand to the receptor,
        regenerating the biosensor,
        bringing into contact a second sample containing the ligand in a second concentration to be determined with the receptor such that at least one ligand can bind to the receptor and can form a ligand-receptor complex with said receptor,
        measuring at least one second value that is dependent on the binding of the ligand to the receptor,
    and, determining the second concentration based on at least in part the measured values and the known first concentration.

* * * * *